(12) United States Patent
Kayyali et al.

(10) Patent No.: US 8,424,527 B1
(45) Date of Patent: Apr. 23, 2013

(54) UNIQUE DEVICE FOR DETERMINING AIRWAY OBSTRUCTIONS

(75) Inventors: Hani Kayyali, Shaker Heights, OH (US); Brian M. Kolkowski, Leroy, OH (US)

(73) Assignee: Cleveland Medical Devices Inc., Cleveland, OH (US)

( * ) Notice: Subject to any disclaimer, the term of this patent is extended or adjusted under 35 U.S.C. 154(b) by 1224 days.

(21) Appl. No.: 12/231,741

(22) Filed: Sep. 5, 2008

(51) Int. Cl.
*A61M 16/00* (2006.01)
*A61M 15/00* (2006.01)

(52) U.S. Cl.
USPC ............. 128/206.21; 128/204.23; 128/200.24

(58) Field of Classification Search ............. 128/200.24, 128/206.21, 206.22, 204.18, 204.23
See application file for complete search history.

(56) References Cited

U.S. PATENT DOCUMENTS

| | | | | |
|---|---|---|---|---|
| 3,990,435 A | * | 11/1976 | Murphy | 600/529 |
| 4,094,304 A | * | 6/1978 | Wright, Jr. | 600/552 |
| 4,197,856 A | * | 4/1980 | Northrop | 600/453 |
| 4,326,416 A | * | 4/1982 | Fredberg | 600/533 |
| 4,672,977 A | * | 6/1987 | Kroll | 600/528 |
| 4,830,015 A | * | 5/1989 | Okazaki | 600/442 |
| 4,982,738 A | * | 1/1991 | Griebel | 600/483 |
| 5,165,417 A | * | 11/1992 | Murphy, Jr. | 600/529 |
| 5,199,424 A | * | 4/1993 | Sullivan et al. | 128/204.18 |
| 5,239,997 A | * | 8/1993 | Guarino et al. | 600/587 |
| 5,259,373 A | * | 11/1993 | Gruenke et al. | 128/204.23 |
| 5,311,875 A | * | 5/1994 | Stasz | 600/537 |
| 5,316,002 A | * | 5/1994 | Jackson et al. | 600/463 |
| 5,318,038 A | * | 6/1994 | Jackson et al. | 600/533 |
| 5,361,767 A | * | 11/1994 | Yukov | 600/442 |
| 5,417,215 A | * | 5/1995 | Evans et al. | 600/442 |
| 5,485,841 A | * | 1/1996 | Watkin et al. | 600/437 |
| 5,509,414 A | | 4/1996 | Hok | |
| 5,588,439 A | * | 12/1996 | Hollub | 600/534 |
| 5,620,004 A | * | 4/1997 | Johansen | 600/529 |
| 5,666,960 A | * | 9/1997 | Fredberg et al. | 600/529 |
| 5,704,345 A | | 1/1998 | Berthon-Jones | |
| 5,746,699 A | * | 5/1998 | Fredberg et al. | 600/529 |
| 5,823,965 A | | 10/1998 | Rasmussen | |
| 5,844,997 A | * | 12/1998 | Murphy, Jr. | 381/92 |
| 5,882,314 A | * | 3/1999 | Fredberg et al. | 600/529 |
| 5,902,237 A | | 5/1999 | Glass | |
| 5,919,139 A | * | 7/1999 | Lin | 600/443 |
| 6,045,514 A | * | 4/2000 | Raviv et al. | 600/529 |
| 6,058,932 A | * | 5/2000 | Hughes | 128/200.24 |
| 6,139,505 A | * | 10/2000 | Murphy | 600/532 |
| 6,142,952 A | * | 11/2000 | Behbehani et al. | 600/533 |
| 6,213,955 B1 | * | 4/2001 | Karakasoglu et al. | 600/529 |
| 6,241,683 B1 | * | 6/2001 | Macklem et al. | 600/529 |
| 6,261,238 B1 | * | 7/2001 | Gavriely | 600/532 |
| 6,379,311 B1 | | 4/2002 | Gaumond et al. | |

(Continued)

*Primary Examiner* — Stephen Crow
(74) *Attorney, Agent, or Firm* — Brian Kolkowski

(57) ABSTRACT

The present invention is related to a device for acoustically monitoring a subject's airway to determine airway obstruction(s) and their location(s). The device is particularly useful when performing sleep analysis and sleep therapy, but is also highly useful in determining airway obstructions of any subject when the subject is sleeping or otherwise unconscious, and can further be used in certain applications when the subject is awake or conscious. The device, in its simplest form, is comprised of a supporting body (e.g. a mask, mouthpiece, or nasal cannula) used to position at least one acoustic generator and at least one acoustic sensor at a location essentially proximal to a subject's airway, the acoustic generator and acoustic sensor generating and/or sensing sound waves useful in determining obstruction(s) and their location(s) within the airway of a subject.

19 Claims, 6 Drawing Sheets

U.S. PATENT DOCUMENTS

| | | | |
|---|---|---|---|
| 6,383,142 B1* | 5/2002 | Gavriely | 600/529 |
| 6,394,967 B1* | 5/2002 | Murphy | 600/586 |
| 6,440,083 B1* | 8/2002 | Fredberg et al. | 600/533 |
| 6,443,907 B1* | 9/2002 | Mansy et al. | 600/529 |
| 6,454,724 B1* | 9/2002 | Greene | 600/534 |
| 6,491,641 B1* | 12/2002 | Rasmussen | 600/529 |
| 6,517,497 B2* | 2/2003 | Rymut et al. | 600/538 |
| 6,709,404 B1 | 3/2004 | Creedon et al. | |
| 6,811,538 B2* | 11/2004 | Westbrook et al. | 600/529 |
| 7,617,821 B2* | 11/2009 | Hughes | 128/200.24 |
| 7,794,399 B2 | 9/2010 | Singh | |
| 2002/0002327 A1* | 1/2002 | Grant et al. | 600/324 |
| 2002/0014235 A1* | 2/2002 | Rogers et al. | 128/200.24 |
| 2002/0183642 A1* | 12/2002 | Murphy | 600/532 |
| 2002/0193697 A1* | 12/2002 | Cho et al. | 600/529 |
| 2003/0045806 A1* | 3/2003 | Brydon | 600/534 |
| 2004/0010202 A1* | 1/2004 | Nakatani et al. | 600/529 |
| 2004/0059240 A1* | 3/2004 | Cho et al. | 600/532 |
| 2004/0069304 A1* | 4/2004 | Jam | 128/204.18 |
| 2004/0236241 A1* | 11/2004 | Murphy | 600/529 |
| 2004/0254493 A1* | 12/2004 | Chervin et al. | 600/544 |
| 2005/0005935 A1* | 1/2005 | Gradon | 128/204.18 |
| 2005/0020932 A1* | 1/2005 | Haberland et al. | 600/538 |
| 2005/0027207 A1* | 2/2005 | Westbrook et al. | 600/529 |
| 2005/0043645 A1* | 2/2005 | Ono et al. | 600/529 |
| 2006/0037615 A1 | 2/2006 | Wilkinson et al. | |
| 2006/0241510 A1 | 10/2006 | Halperin et al. | |
| 2007/0032353 A1* | 2/2007 | Wilkins et al. | 482/54 |
| 2007/0239056 A1 | 10/2007 | Moore | |
| 2011/0066058 A1 | 3/2011 | Singh | |

* cited by examiner

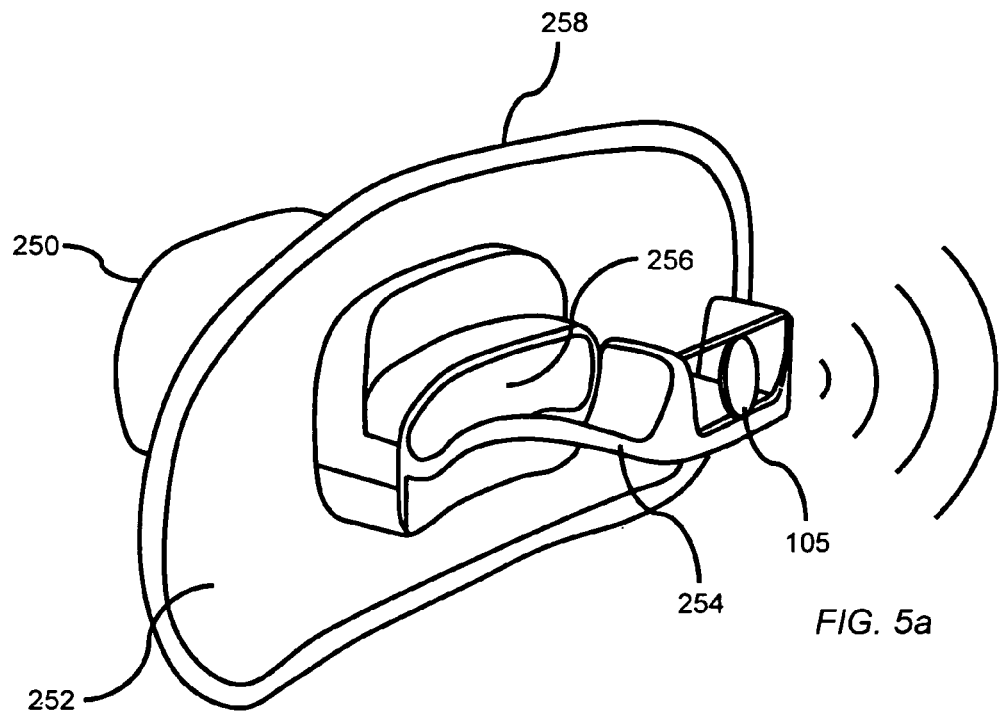
*FIG. 5a*
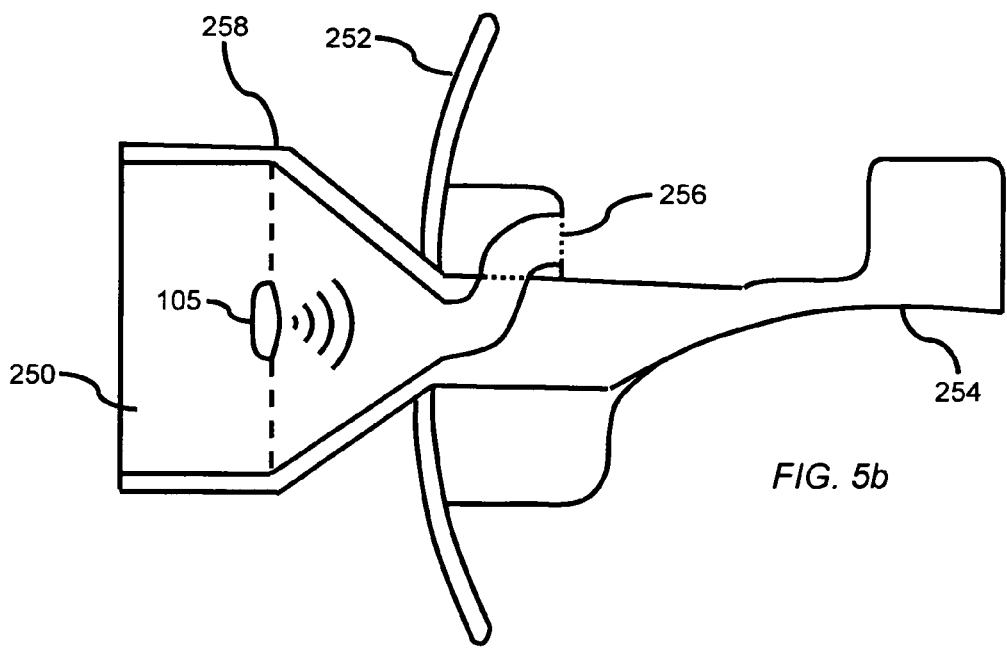
*FIG. 5b*
*FIG. 5*

UNIQUE DEVICE FOR DETERMINING AIRWAY OBSTRUCTIONS

BACKGROUND OF THE INVENTION

1. Field of Use

The present invention is related to a novel and unique device for acoustically monitoring a subject's airway to determine airway obstruction(s) and their location(s). The device is particularly useful when performing sleep analysis and sleep therapy, but is also highly useful in determining airway obstructions of any subject when the subject is sleeping or otherwise unconscious, and can further be used in certain applications when the subject is awake or conscious. The device, in its simplest form, is comprised of a supporting body (e.g. a mask, mouthpiece, or nasal cannula) used to position at least one acoustic generator and at least one acoustic sensor at a location essentially proximal to a subject's airway, the acoustic generator and acoustic sensor generating and/or sensing sound waves useful in determining obstruction(s) and their location(s) within the airway of a subject.

2. Technology Review

Because of the vital role that the respiratory system plays in human health and physiological function, monitoring of a subject's airway is an important part of providing quality health care. Specifically, determination and monitoring of obstructions and their locations within a subject's airway is a critical and useful step in many health care applications. Among the most critical and useful applications are airway monitoring during sleep analysis and therapy as well as during procedures involving the use of sedatives or general anesthesia wherein a subject is unconscious.

Currently, a number of imaging modalities exist which can be used to examine a subject's airway, including cephalometry, computed tomography and pharyngometry. However, because of the temporal limitations and the methods and nature of the equipment required to perform these procedures, they cannot practically be used to monitor a subject's airway while the subject is asleep or unconscious. Other imaging methods exist which may be used over longer time periods and/or while a subject is asleep or unconscious, such as sleep endoscopy and manometry. However, these methods are costly, ineffective and invasive, as they require placement of nasal catheters or endoscopes into the pharynx of a subject under local anesthetic for prolonged periods of time.

Notwithstanding the many methods available to image or monitor a subject's airway, currently, none of these methods are viable solutions to providing a way to accurately and conveniently monitor and localize airway obstructions while a subject is asleep or unconscious.

To address these shortcomings, it is therefore an object of the present invention to provide a device for convenient, non-invasive monitoring of airway state while a subject is asleep or unconscious. It is another object of the present invention to provide a device wherein at least one acoustic generator and at least one acoustic sensor are placed essentially proximal to the airway of a subject to collect information on the nature and location of obstructive tissue within a subject's airway. It is another object of the present invention to provide a device by which information pertaining to the nature and location of obstructive tissue within a subject's airway can be obtained and used in surgical planning, therapeutic planning, diagnosis, and the like. It is still another object of the present invention to provide a device wherein acoustic monitoring of obstruction(s) and their location(s) within a subject's airway is used in connection with, or controlled by, a respiratory therapy or respiratory assist device.

SUMMARY OF THE INVENTION

The present invention is related to a novel and unique device for acoustically monitoring a subject's airway to determine airway obstruction(s) and their location(s). The device is particularly useful when performing sleep analysis and sleep therapy, but is also highly useful in determining airway obstructions of any subject when the subject is sleeping or otherwise unconscious, and can further be used in certain applications when the subject is awake or conscious. The device, in its simplest form, is comprised of a supporting body (e.g. a mask, mouthpiece, or nasal cannula) used to position at least one acoustic generator and at least one acoustic sensor at a location essentially proximal to a subject's airway, the acoustic generator and acoustic sensor generating and/or sensing sound waves useful in determining obstruction(s) and their location(s) within the airway of a subject.

The device of the present invention is particularly useful in a number of applications. These applications include, but are not limited to, testing and/or treating a subject with a respiratory disorder, more particularly an obstructive sleep respiratory disorder. The device of the present invention is further particularly useful in monitoring airway patency of a subject who is asleep or unconscious. The device is also useful in providing acoustic data pertaining the state of subject's airway, which can be used in diagnosing a subject's respiratory disorder. A further useful application of the device includes the collection of acoustic data to localize an airway obstruction and, using this data, at least in part, to determine tissue to be surgically removed from a subject's airway or to determine a proper therapeutic approach. A further useful application of the device includes the collection of acoustic data to localize an airway obstruction and, using this data, at least in part, to determine tissue or anatomical structures in the mouth to be shifted by oral appliances to determine a proper therapeutic approach. The device of the present invention further includes any useful applications not listed, which will be apparent to those skilled in the art.

The device of the present invention includes a number of features which enhance the device over other similar existing devices. These features include but are not limited to: the non-invasive use of the device while a subject is asleep or unconscious, to acoustically monitor the state of the subject's airway; the use of a mask to position both an acoustic sensor and acoustic generator at a location essentially proximal to a subject's airway and to perform acoustic monitoring of obstruction(s) within an airway of a subject; the use of a mask to position both an acoustic sensor and acoustic generator at a location essentially proximal to a subject's airway while also providing a connection to a respiratory therapy or respiratory assist device; the use of a mouthpiece to position at least one acoustic generator and at least one acoustic sensor at a location essentially proximal to a subject's airway; the use of a nasal cannula to position at least one acoustic sensor and at least one acoustic generator at a location essentially proximal to a subject's airway, more specifically, essentially proximal to a subject's nares.

The device of the present invention can also comprise other sensors, and further can be used for compliance purposes. For example, the device can contain a motion or position sensor to further define the diagnostic data developed from the acoustic transducer or for the separate purpose of determining whether the subject has been complying with treatments related to wearing the device. One example would be a device containing an acoustic transducer and a motion or position sensor. The device, however, could also merely contain the motion or position sensor by itself. Other sensors that could be used alone or in combination with various embodiments of the present invention include snore sensors, pressure sensors, environmental sensors, physiological recording devices attached or embedded into the device, and the like.

Numerous embodiments of the present invention are disclosed herein, and examples of these embodiments are as follows, these examples are, however, merely exemplary of the various embodiments that are envisioned. In one embodiment, the present invention includes a mouthpiece which is inserted into the mouth of a subject, the body of the mouthpiece capable of fitting between a subject's lips while allowing the subject to breathe regularly through the mouthpiece. The mouthpiece is also used to position at least one acoustic generator and at least one acoustic sensor at a location essentially proximal to the subject's airway for use in acoustically monitoring a subject's airway for obstructions. The mouthpiece of the present invention can be used alone as a diagnostic tool or in connection with a respiratory therapy device wherein the respiratory therapy device is attached to the mouthpiece.

In another embodiment, the present invention includes a nasal cannula comprised of a tubular body and two nasal prongs which are inserted into the nares of a subject and used to deliver oxygen or other gases to the nasal passages. The nasal cannula is further comprised of at least one acoustic generator and at least one acoustic sensor, preferably positioned near the nasal prongs, and used to acoustically monitor the subject's airway for obstructions.

In still another embodiment, the present invention includes a mask used to position at least one acoustic generator and one acoustic sensor at a location essentially proximal to a subject's airway. The mask can be a nose mask, an oral mask, or a face mask. In various embodiments, the mask is used alone as a diagnostic tool and can include vents or airways to allow the subject to breathe regularly through the mask when it is worn. In other embodiments, the mask can include a point of connection to a respiratory device for use in applications involving respiratory therapy, assisted breathing, and the like.

Additional features and advantages of the invention will be set forth in the detailed description that follows, and in part will be readily apparent to those skilled in the art from that description or recognized by practicing the invention as described herein, including the detailed description that follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, illustrate various embodiments of the invention and, together with the description, serve to explain the principles and operation of the invention.

BRIEF DESCRIPTION OF THE DRAWINGS

FIG. 5 a) Perspective view of one embodiment of a mouthpiece used in the present invention also showing positioning of acoustic transducer on the mouthpiece, and b) a cross-sectional side view of the mouthpiece showing alternate placement of acoustic transducer.

DESCRIPTION OF THE PREFERRED EMBODIMENTS

Figure 1:
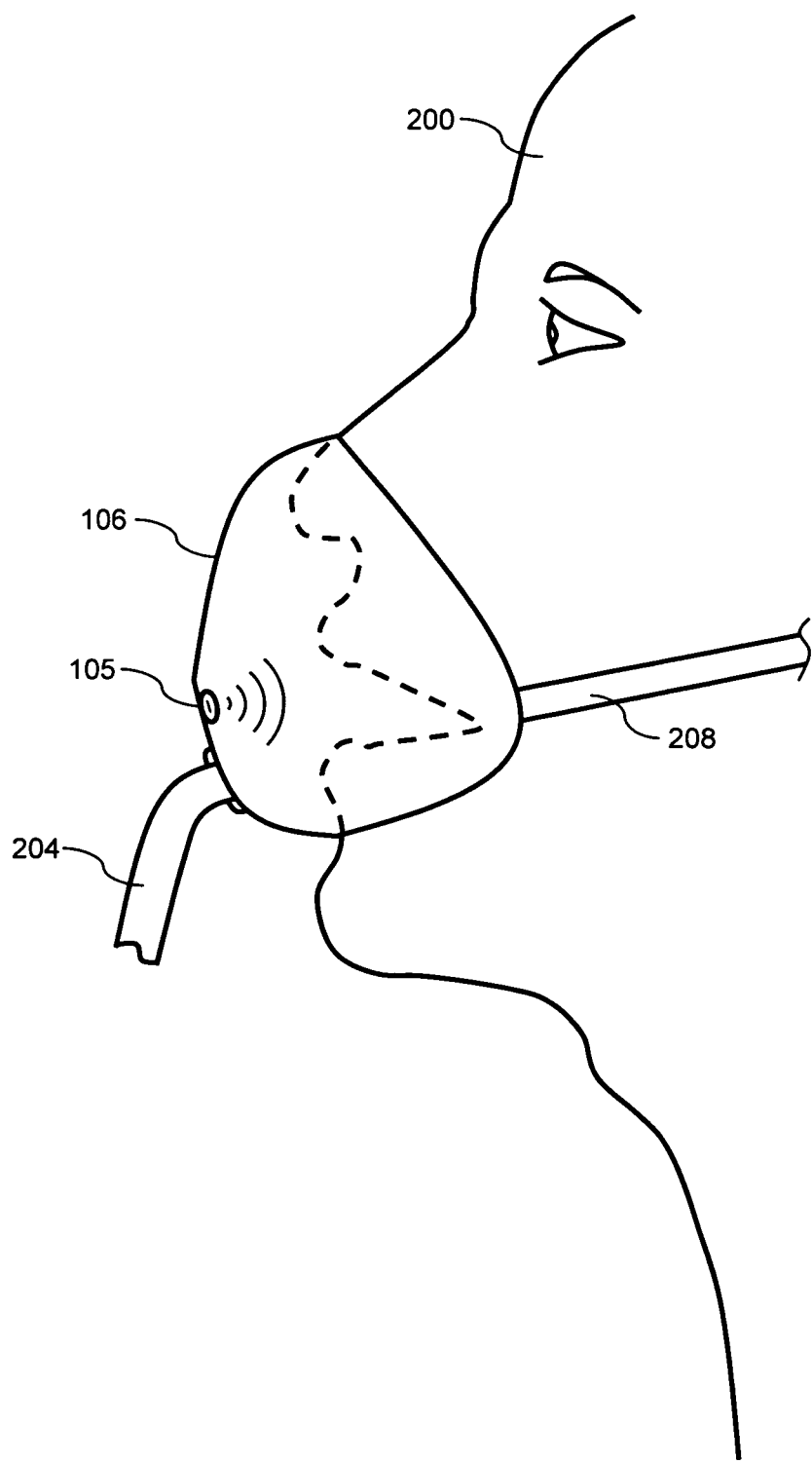
FIG. 1 Partial side view of a subject wearing a face mask with acoustic transducer used in one embodiment of the present invention.

The present invention is related to a novel and unique device for acoustically monitoring a subject's airway to determine airway obstruction(s) and their location(s). The device is particularly useful when performing sleep analysis and sleep therapy, but is also highly useful in determining airway obstructions of any subject when the subject is sleeping or otherwise unconscious, and can further be used in certain applications when the subject is awake or conscious. The device, in its simplest form, is comprised of a supporting body (e.g. a mask, mouthpiece, or nasal cannula) used to position at least one acoustic generator and at least one acoustic sensor at a location essentially proximal to a subject's airway, the acoustic generator and acoustic sensor generating and/or sensing sound waves useful in determining obstruction(s) and their location(s) within the airway of a subject.

Various embodiments of the present invention, use an acoustic transducer to generate or sense sound waves. Other embodiments contain or include other sensors. In certain embodiments, the acoustic transducer used as part of the invention is an acoustic sensor. Preferably, this sensor is capable of converting sound waves into electrical signals for use in examination and analysis of acoustic data. In other embodiments of the present invention, the acoustic transducer used as part of the invention is an acoustic generator. Preferably, this generator is capable of converting electrical signals into sound waves, and is capable of producing variable output dependent upon electrical input. In still other preferable embodiments, the acoustic transducer is capable of acting as both an acoustic sensor and an acoustic generator and is used to produce and emit sound waves and subsequently measure reflections of the emitted sound waves.

Acoustic transducers used in the present invention can be any type known in the art. One example of such a transducer is an electro-acoustic transducer, which uses a pressure-sensitive diaphragm connected to various electrical components to measure sound waves, produce sound waves, or both. Another example of an acoustic transducer useful in the present invention is a piezoelectric acoustic transducer which uses a piezoelectric crystal to convert sound waves into electrical signals and electrical signals to sound waves. It is envisioned that the range of signals capable of being generated and sensed by the acoustic transducers will extend from audible frequencies to ultrasonic frequencies, preferably, from about 20 Hz to about 20 MHz, and more preferably at least about 20 kHz. Due to the range of envisioned frequencies, various embodiments of the invention may use different models and/or types of acoustic transducers. Preferably, the acoustic generator and acoustic sensor are of small enough dimensions that they can be conveniently placed in a mask, mouthpiece, cannula or the like for use in or near a subject's mouth or nose. The above examples are given only as representative illustrations, and are not intended to limit the present invention.

Various embodiments of the present invention use acoustic transducer(s) placed in or on a supporting body such as a mask, cannula or mouthpiece in order to generate and/or measure various acoustic signals from a location essentially proximal to a subject's airway. By essentially proximal to a subject's airway it is meant that the acoustic transducer is placed either inside of a subject's mouth or nose or within about 12 inches of the outside of the subject's mouth or nose, more preferably within about 8 inches of the outside of the subject's mouth or nose, even more preferably within about 4 inches of the outside of a subject's mouth or nose and most preferably within about 2 inches of the outside of a subject's mouth or nose. By positioning the acoustic transducer(s) essentially proximal to a subject's airway, attenuation of sound waves is minimized and ease of adaptation of acoustic variables to changing conditions, such as opening and closing of the mouth, is increased. Further, by positioning the acoustic transducer at a location essentially proximal to a subject's airway it is easier and more effective to use higher frequency sound waves, which increase resolution of the location and characteristics of the obstruction(s) within a subject's airway.

In various embodiments of the present invention, placement of an acoustic transducer in or on the supporting body (mask, mouthpiece, cannula etc.) can be done in such a way that the acoustic transducer is permanently connected to, or embedded in, the supporting body. More preferably, however, placement of the acoustic transducer on the supporting body is done so that the transducer is easily removable and interchangeable with other types of transducers or electronic components. For example, certain applications may be better suited for use with an acoustic transducer capable of generating lower frequency sound waves whereas other applications may require the use of an acoustic transducer capable of generating ultrasonic waves. By making the acoustic transducer easily removable and interchangeable, adaptation of the device to changing applications such as these becomes more simple and cost-effective.

In its simplest form, acoustic monitoring of a subject's airway to determine obstruction(s) and their location(s) is performed by emitting sound waves into the subject's airway by supplying an electrical signal to an acoustic generator and subsequent measurement and observation of the behavior of these waves using an acoustic sensor. Specifically, as sound waves travel down the airway, some of the waves are reflected as they contact various structures within the airway. These reflected waves can be converted to electrical signals by the acoustic sensor which can then be analyzed to provide information about obstruction(s) and their location(s) within the subject's airway.

Analysis of acoustic data can be performed by any device equipped with appropriate data acquisition and processing hardware. Examples of such devices may include sleep analysis devices, respiratory therapy devices (e.g. a continuous positive airway pressure device), notebook computers, or the like. Communication and transfer of acoustic data can be accomplished using a wired or wireless connection from an acoustic transducer. If a wired connection is used, the wires are preferably embedded within a supporting body, such as a mask body and/or an air hose attached to a respiratory device. Optionally, the connecting wires may be left untethered. In its simplest application, acoustic data can provide a determination of whether a subject's airway is either open or closed. In other applications, the acoustic data can undergo more complex analysis to provide information on the degree, dynamic and location of airway obstruction(s). In still other applications, acoustic data can be used to calculate the cross-sectional area of the airway as a function of distance.

Various embodiments of the present invention use a mask equipped with at least one acoustic generator and at least one acoustic sensor to position the acoustic generator and acoustic sensor at a location essentially proximal to a subject's airway. Preferably, the mask is capable of essentially conforming to a subject's facial features. By essentially conforming to a subject's facial features it is meant that the mask is shaped to approximate the contours of the nose, mouth, and/or chin of a human subject. The mask can be of various types including, but not limited to, a face mask, covering both the nose and mouth of a subject, an oral mask, covering only the mouth of a subject, or a nasal mask, covering only a subject's nose. The body of the mask is preferably comprised of a rigid or semi-rigid material such as a thermoplastic or thermoset polymer but can be, in certain embodiments, wholly or partly comprised of soft, rubber-like materials such as silicon polymers and certain elastomers. Preferably, each type of mask (i.e. face mask, oral mask, or nose mask) is capable of being used either alone as a diagnostic tool or in conjunction with a respiratory therapy or respiratory assist device as both a diagnostic and therapeutic tool. When used alone, the mask preferably includes airways, ports, or vents to allow a subject to breathe regularly while wearing the mask. If used in conjunction with a respiratory therapy or respiratory assist device the mask preferably includes a point of attachment for an air hose and is preferably structured so as to seal tightly against a subject's face to allow effective and efficient use of the respiratory therapy or respiratory assist device.

One example of a respiratory device with which the mask could be used is a continuous positive airway pressure (CPAP) device. In one embodiment, use of the mask with such a device could allow correlation of positive airway pressure with degree and location of obstruction(s) within a subject's airway, providing means for more effective treatment and diagnosis of obstructive airway disorders.

Where the mask, mouthpiece or cannula are attached to an air supply such as a positive airway pressure device (PAP) or a continuous positive airway pressure device (CPAP), the transducers or sensors can be connected to the therapeutic device by wires that either trail the air hose or are directly embedded in such hose. In addition, the transducer or sensor can use wireless technology to transmit data between the mask, mouthpiece or cannula to a communication station or monitor or the therapeutic device.

Placement of the acoustic transducer in the mask will vary, depending upon the type of mask and application for which it is used. Preferably, if the mask is an oral or face mask, the acoustic transducer(s) are placed directly in front of the mouth and as near to the mouth as is practical. If the mask is a nasal mask, the acoustic transducer(s) are preferably placed directly beneath opening(s) of the nares and as near to the opening of the nares as possible without unduly restricting a subject's respiration.

Various embodiments of the present invention use a mouthpiece, placed at least partially within a subject's mouth, to position at least one acoustic generator and at least one acoustic sensor at a location essentially proximal to a subject's airway. Preferably, the mouthpiece is comprised of a mouthpiece body capable of fitting between a subject's lips, a tongue-depressing portion to prevent the tongue from obstructing acoustic transmission, an air port extending outside of the mouth to allow regular breathing while using the device, and flanges which are placed either intra-orally between the inner surface of a subject's lips and a subject's gums or extra-orally, contacting the outside surface of a subject's lips in order to keep the device in its proper position and provide a seal between the subject's mouth and the mask when the mouthpiece is used with a respiratory device. The body of the mouthpiece is preferably comprised of a combination of rigid or semi-rigid materials and soft, pliable materials in order to increase comfort of the subject when using the device. For example, the flanges of the mouthpiece that contact the subject's gums and inner surface of the subject's lips are preferably comprised of a soft, pliable material, while the tongue-depressing portion of the mouthpiece is preferably composed of a rigid material to resist deflection from the pressure of contacting the tongue.

In one embodiment, the portion of the air port of the mouthpiece which extends outside of the mouth can optionally be used to connect the mouthpiece to the air hose of a respiratory therapy or respiratory assist device. In this embodiment, the flanges of the mouthpiece serve the function of providing a seal between the mouthpiece and the subject's mouth, allowing for effective and efficient use of the respiratory therapy device.

Positioning of the acoustic transducer within the device can vary depending upon desired performance or application. In certain applications, the acoustic transducer may be placed near the end of the tongue-depressing portion of the mouthpiece in order to position the acoustic transducer as near to the airway as possible, while in other applications the acoustic transducer may be placed outside the mouth in the external portion of the air port of the mouthpiece.

When using the mouthpiece described herein, it is not required that the subject breathe through the mouthpiece. Optionally, the subject may breathe through his or her nose. Accordingly, in certain embodiments, the mouthpiece need not include an air port to allow breathing through the mouth, but can be placed wholly within the mouth while the subject breathes through his or her nose with only the wires for connection to the acoustic transducer(s) being external to the mouth.

Still various other embodiments of the present invention use a nasal cannula to position acoustic transducer(s) at a location essentially proximal to a subject's airway. The nasal cannula is preferably comprised of a tubular body capable of connection to a source of pressurized gas or air, and two nasal prongs extending essentially perpendicularly from the tubular body for insertion into a subject's flares. By essentially perpendicular, it is meant that the long axis of the nasal prongs is preferably oriented at an angle between 45° and 135° to the long axis of the body of the cannula. The body and nasal prongs of the nasal cannula can be comprised of any material capable of maintaining a tubular shape. Examples of such materials include, but are not limited to thermoplastic and thermoset polymers and lightweight metals, such as aluminum and various titanium alloys.

Although capable of using a single acoustic transducer, the nasal cannula preferably uses at least two acoustic transducers, with one transducer being placed in the tubular body directly beneath each of the two nasal prongs. In various embodiments, these transducers can function as various combinations of acoustic sensors, acoustic generators, or as both an acoustic sensor and acoustic generator. Acoustic transducers in this embodiment can also be placed in other locations including locations within the air hose at varying distance from the nasal prongs.

Turning now to a description of the figures, FIG. 1 is a partial side view of a subject 200 wearing one embodiment of the mask 106 of the present invention used to position an acoustic transducer 105 near the subject's airway. The acoustic transducer 105 shown here is preferably capable of both generating and sensing sound waves, eliminating the need for a separate acoustic generator and acoustic sensor. The mask 106 shown here includes an air hose 204 whereby the mask may be connected to a respiratory therapy or respiratory assist device. The mask preferably forms a tight seal against the subject's face and is held snug over the subject's mouth and nose by a strap 208 used to secure the mask to the subject 200. The mask 106 shown in FIG. 1 is preferably used during a respiratory therapy or treatment procedure in which acoustic data collected using the acoustic transducer 105 is used, at least in part, to quantify the effectiveness of the therapy or treatment and to plan future treatment or intervention on behalf of the subject. Acoustic data collected using this embodiment can be stored and/or analyzed using any of the aforementioned devices for storage and analysis.

Figure 2:
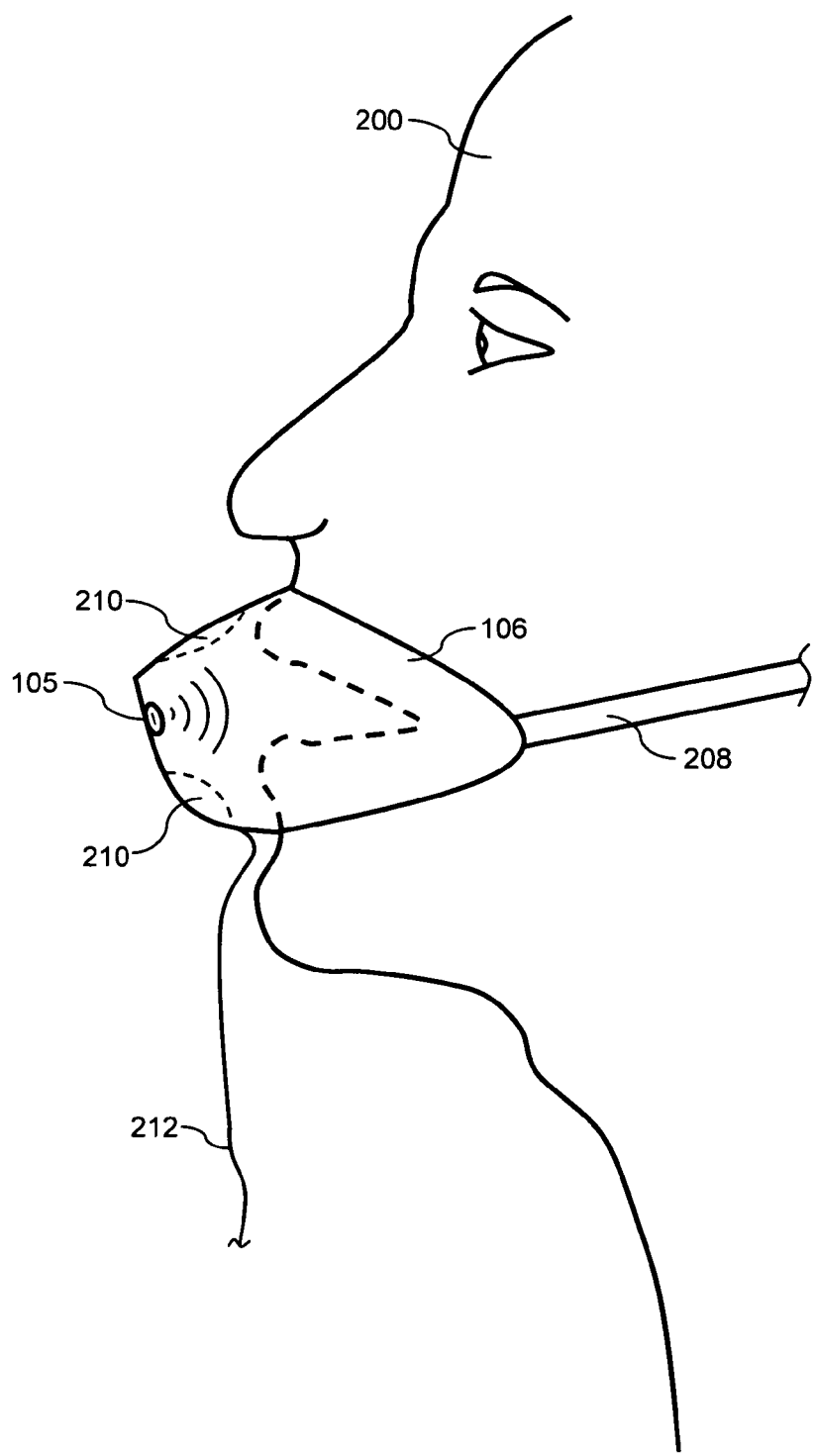
FIG. 2 Partial side view of a subject wearing an oral mask with acoustic transducer used in another embodiment of the present invention.

FIG. 2 shows another partial side view of a subject 200 wearing one embodiment of the present invention wherein the mask 106 used to support and position the acoustic transducer 105 near the airway of the subject 200 is an oral mask, covering only the mouth of the subject. In this embodiment, ports, vents or airways 210 are placed in the mask to allow the subject 200 to breathe regularly while wearing the mask. The mask is held tightly over the subject's mouth by a strap 208 used to secure the mask to the subject 200. As shown here, generation and recording of sound waves emitted into the subject's airway is transmitted to an external device (not shown) for storage and/or analysis using a hard-wired connection 212 from the acoustic transducer 105. However, transmission of data need not occur using a hard-wired connection, and in other embodiments wireless transmission of data, in whole or in part, may also be used. As noted above, storage and/or analysis of acoustic data can be performed by any device equipped with appropriate data acquisition and processing hardware.

Figure 3:
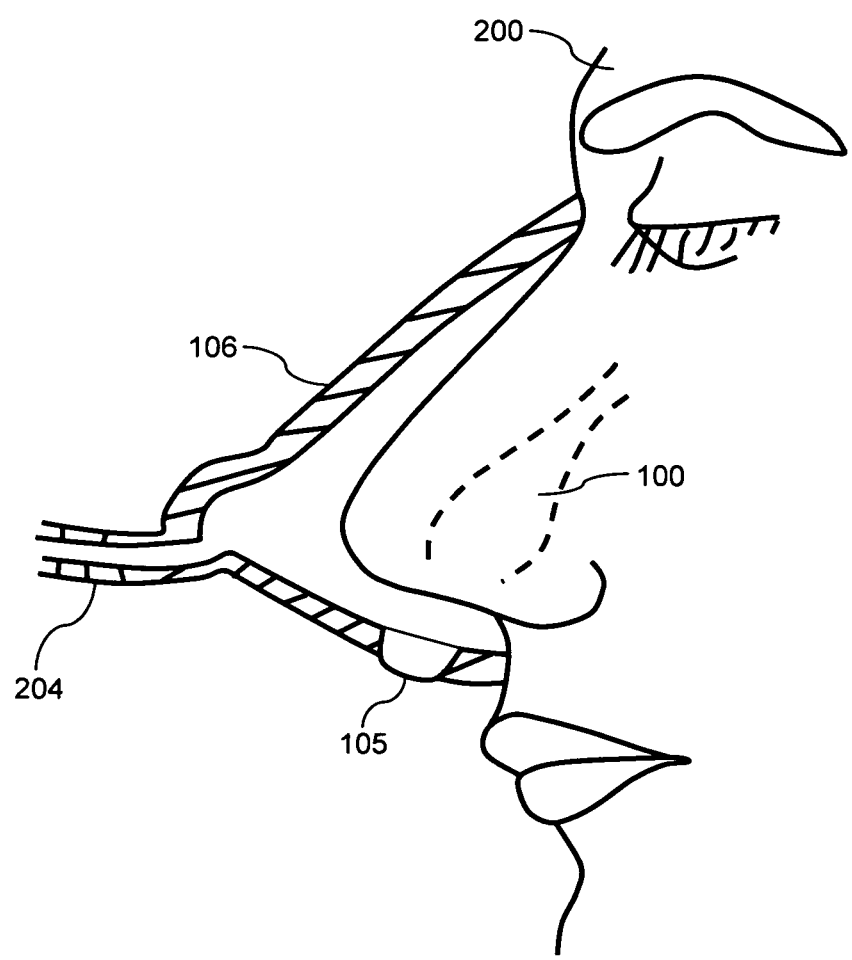
FIG. 3 Partial side view of a subject wearing a nose mask with acoustic transducer used in still another embodiment of the present invention.

FIG. 3 shows still another partial side view of a subject 200 wearing one embodiment of the mask of the present invention. The mask 106 shown here is a nasal mask, covering only the nose of the subject 200. Here, as in FIG. 1, the mask 106 includes an air hose 204 for connection to a respiratory therapy or respiratory assist device (not shown). The mask preferably forms a tight seal against the subject's skin to allow effective and efficient use of the respiratory therapy device. In this embodiment, the acoustic transducer 105 is shown positioned near the nares 100 in order to direct emitted sound waves into the subject's airway and more easily detect reflected waves as they exit the subject's airway. As above, acoustic data collected using this embodiment can be stored and/or analyzed using any of the aforementioned devices for storage and analysis.

Figure 4:
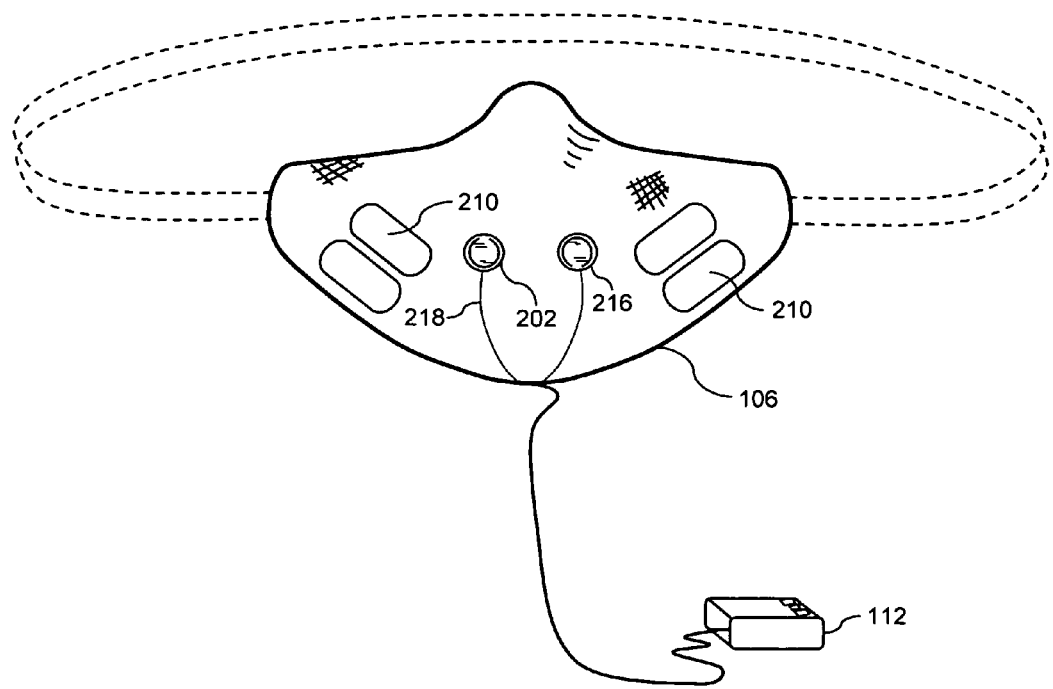
FIG. 4 Front view of one embodiment of a mask used with the present invention wherein the mask includes an independent acoustic generator and acoustic sensor.

Referring now to FIG. 4, there is shown a front view of one embodiment of the mask 106 of the present invention. Here, a separate acoustic sensor 202 and acoustic generator 216 are used to conduct acoustic monitoring of a subject's airway for obstructions. Wires 218 used to connect the acoustic sensor 202 and acoustic generator 216 to an external data collection and analysis device 112 can be embedded in the mask (as shown here) or attached simply to the acoustic sensor and acoustic generator while not being embedded in the mask. Though not shown here, in one envisioned embodiment, the acoustic sensor and acoustic generator are preferably secured in the mask in such a way that they can be easily removed and replaced with sensors and or generators of a different type but similar dimensions for use under varying conditions or applications. The mask 106 shown in FIG. 4 includes ports, vents or airways 210 to allow unhindered breathing by the subject, while the mask is worn. Optionally, however, the mask could just as easily include an air hose for connection to a respiratory therapy or respiratory assist device in place of ports or vents for applications involving the use of respiratory treatment or therapy.

Shown in FIG. 5a is a perspective view of a mouthpiece 258 used in one embodiment of the present invention to position an acoustic transducer 105 at a location proximal to a subject's airway. In this embodiment, the mouthpiece includes a flange 252 which is inserted into the mouth in the space between the inner surface of the subject's lips and the subject's gums, creating a seal with the inner surface of the lips of the subject. In other embodiments, the flange 252 can be positioned to be used outside of the mouth, contacting only the exterior surface of the lips of the subject. In still other embodiments, the flange 252 need not be present at all. The mouthpiece also includes an air port 256 which passes through the lips of the subject, allowing the subject to breathe normally while using the mouthpiece. The mouthpiece further includes a tongue depressing portion 254 to prevent the tongue from obstructing the travel of sound waves through the airway of the subject. As shown in FIG. 5a, the acoustic transducer 105 is positioned at the end of the tongue depressing portion of the mouthpiece 254, allowing acoustic monitoring of the subject's airway for obstructions to be conducted as near to the subject's airway as possible.

FIG. 5b is a cross-sectional side view of the mouthpiece 258, illustrating an optional placement location for the acoustic transducer 105. As shown here, the acoustic transducer can optionally be placed outside of the oral cavity in the external portion of the air port of the mouth piece 250. Further, though not shown, in certain embodiments the external portion of the air port of the mouthpiece 250 could also be used to provide a connection to a respiratory therapy or respiratory assist device.

Figure 6:
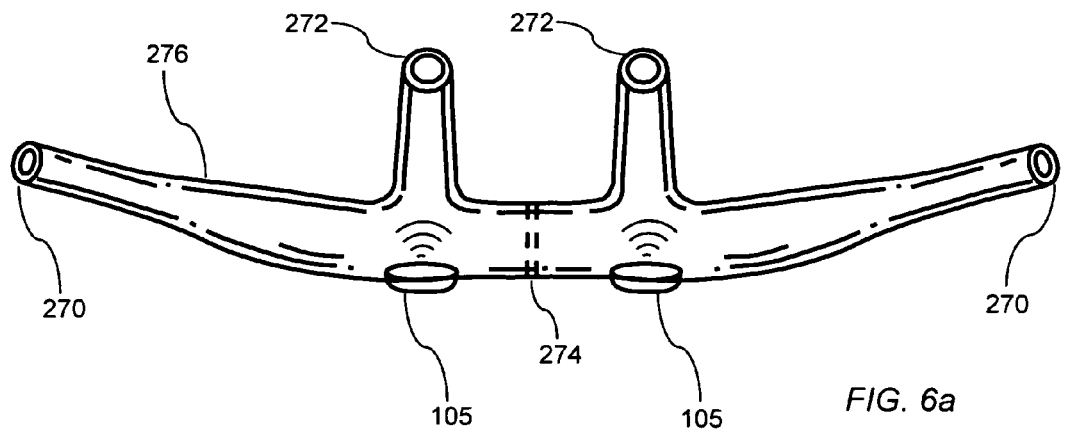
FIG. 6 a) Perspective view of one embodiment of a nasal cannula used in the present invention showing placement of acoustic sensors on the cannula, and b) a partial side view of a subject using the nasal cannula.
Figure 6:
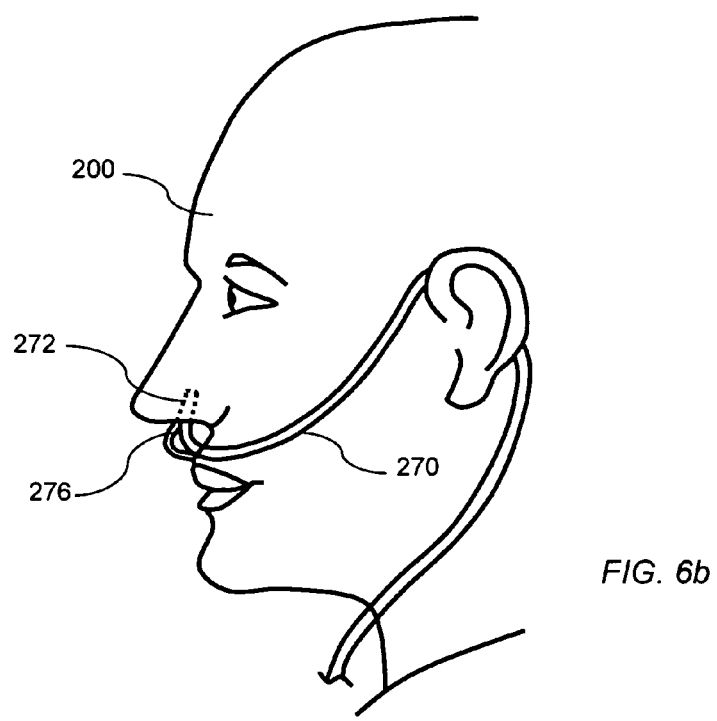

Turning now to FIG. 6, there is shown one embodiment of a nasal cannula used in the present invention. The nasal cannula 276 shown in FIG. 6a is comprised of two nasal prongs 272 which are inserted into the nares (as shown in FIG. 6b) during use of the device and two openings 270 on each end for connection to a source of pressurized gas or air. The nasal cannula 276 shown here further includes two acoustic transducers 105 which are attached to the cannula beneath the nasal prongs 272 in order to direct emitted sound waves into the subject's airway and/or more easily detect reflected waves as they exit the subject's airway through the nares. In various specific embodiments, the acoustic transducers 105 may serve to function respectively as one acoustic generator and one acoustic sensor, two acoustic sensors, two acoustic generators, and, most preferably, two transducers capable of both generating and sensing sound waves. Optionally, in certain embodiments, a septum 274 may be placed in the cannula between the nasal prongs 272 in order to control airflow and/or acoustic properties of the cannula. FIG. 6b shows a simple schematic of a subject 200 wearing the nasal cannula 276 with the nasal prongs 272 inserted into the nares and the air hose 270 routed behind the subject's ears and connected to a source of pressurized gas or air (not shown).

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

We claim:

1. A mask for acoustic monitoring of obstruction(s) within an airway of a subject comprising: a mask having a body, the body of the mask capable of essentially conforming to a subject's facial features while positioned about the subject's mouth and/or nose and; an acoustic generator and sensor positioned in the mask to be essentially proximal to the subject's mouth or nose, the acoustic generator for generating an acoustic signal, and the acoustic sensor for sensing reflections of the acoustic signal as the acoustic signal is reflected by structures in the subject's upper airway to determine the location of an obstruction within a subject's upper airway; wherein the acoustic generator and the acoustic sensor are comprised of a single acoustic transducer capable of both generating and sensing sound waves.

2. The device of claim 1 wherein said mask further includes vents, ports or airways to allow the subject to breathe regularly while wearing said mask.

3. The device of claim 1 wherein said mask further includes a point of connection to an air hose attached to a continuous positive airway pressure device.

4. The device of claim 1 wherein the acoustic generator and the acoustic sensor are electronically connected to, and/or controlled by a continuous positive airway pressure device, or sleep disorders diagnostic equipment.

5. The device of claim 1 wherein the mask is a face mask, covering both the mouth and nose of the subject.

6. The device of claim 1 wherein the mask is a nose mask, covering only the nose of the subject.

7. The device of claim 1 wherein the mask is an oral mask, covering only the mouth of the subject.

8. The device of claim 1 wherein the single acoustic transducer comprises a piezoelectric acoustic transducer.

9. The device of claim 1 wherein the single acoustic transducer comprises a pressure-sensitive diaphragm connected to appropriate electrical components to allow the diaphragm to both generate an acoustic signal and sense reflections of the generated acoustic signal.

10. A system for acoustic monitoring of obstructions in a subject's upper airway, the system comprising: a mask, the mask comprising a mask body capable of essentially conforming to a subject's facial features, at least one acoustic generator and at least one acoustic sensor integrated into the mask, the at least one acoustic generator for generating an acoustic signal, and the at least one acoustic sensor for sensing reflections of the acoustic signal as the acoustic signal is reflected by structures in the subject's upper airway to determine the location of an obstruction within a subject's upper airway; wherein the acoustic generator and the acoustic sensor are comprised of a single acoustic transducer capable of both generating and sensing sound waves; and a sleep diagnosis device connected to the acoustic generator and acoustic sensor of the mask for generating signals to be output by the acoustic generator and for receiving and storing reflected acoustic signals sensed via the acoustic sensor.

11. The system of claim 10 wherein the sleep diagnosis device is further capable of analyzing the acoustic signals output by the acoustic generator and the reflected acoustic signals sensed by the acoustic sensor to determine a location of an obstruction in the subject's upper airway.

12. The system of claim 10 wherein the mask is a face mask that covers both the mouth and nose of the subject.

13. The system of claim 10 wherein the single acoustic transducer comprises a pressure-sensitive diaphragm connected to appropriate electrical components to allow the transducer to both measure and produce sound waves.

14. The system of claim 10 wherein the single acoustic transducer comprises a piezoelectric acoustic transducer.

15. A method of monitoring obstructions within a subject's upper airway while the subject sleeps, the method comprising: placing a mask on a subject's face, the mask comprising a mask body capable of essentially conforming to a subject's facial features, at least one acoustic generator for generating an acoustic signal and at least one acoustic sensor for sensing reflections of the generated acoustic signal; connecting the at least one acoustic generator and the at least one acoustic sensor to a sleep diagnosis device capable of generating signals to be output by the acoustic generator and receiving and storing reflected acoustic signals sensed via the acoustic sensor while the subject sleeps; and analyzing the generated and reflected acoustic signals to determine the location of an obstruction within a subject's upper airway; wherein the acoustic generator and the acoustic sensor are comprised of a single acoustic transducer capable of both generating an acoustic signal and sensing reflections of the generated signal.

16. The method of claim 15 wherein the mask is a face mask that covers both the mouth and nose of the subject.

17. The method of claim 15 wherein the step of analyzing is performed automatically by a computer.

18. The method of claim 15 wherein the single acoustic transducer comprises a pressure-sensitive diaphragm connected to appropriate electrical components to allow the diaphragm to both measure and produce sound waves.

19. The method of claim 15 wherein the single acoustic transducer comprises a piezoelectric acoustic transducer.

* * * * *